United States Patent [19]

Thomas

[11] Patent Number: 4,798,599

[45] Date of Patent: Jan. 17, 1989

[54] EYE WASHING METHOD AND APPARATUS

[76] Inventor: George Thomas, 10611 99th St. S.W., Tacoma, Wash. 98498

[21] Appl. No.: 567,646

[22] Filed: Jan. 3, 1984

[51] Int. Cl.[4] .................................................. A61M 7/00

[52] U.S. Cl. ..................................... 604/290; 604/297; 604/19

[58] Field of Search ...................... 604/297, 19, 22, 35, 604/27, 28, 30, 46–48, 50, 54, 294–300; 128/20

[56] References Cited

U.S. PATENT DOCUMENTS

| | | | |
|---|---|---|---|
| Re. 28,873 | 6/1976 | Morgan . | |
| 676,379 | 6/1901 | Young . | |
| 1,006,945 | 10/1911 | Houston . | |
| 1,246,971 | 11/1917 | Maier | 604/297 |
| 1,362,682 | 12/1920 | Dayton . | |
| 1,437,435 | 12/1922 | Maier . | |
| 1,900,201 | 3/1933 | Sager . | |
| 2,524,720 | 10/1950 | Watrous . | |
| 2,818,068 | 12/1957 | De Felice . | |
| 3,170,462 | 2/1965 | Hall | 604/298 |
| 3,261,355 | 7/1966 | Burbig . | |
| 3,664,340 | 5/1972 | Morgan . | |
| 4,036,230 | 7/1977 | Adams | 604/294 |
| 4,131,115 | 12/1978 | Peng | 604/297 |
| 4,193,401 | 3/1980 | Marinello . | |

FOREIGN PATENT DOCUMENTS

| | | | |
|---|---|---|---|
| 0213288 | 9/1909 | Fed. Rep. of Germany | 604/297 |
| 0641061 | 8/1950 | United Kingdom | 604/19 |

*Primary Examiner*—Stephen C. Pellegrino
*Attorney, Agent, or Firm*—Delbert J. Barnard

[57] ABSTRACT

An eyecup (10) having a rim portion (14) that conforms to an orbit portion which surrounds an eye (12) on the face of a person is placed over the eye. The eyecup (10) forms a liquid confining chamber (45) adjacent the eye (12). The skin above and below the eye (20, 22) is drawn away from the eye (12), with the eyecup being pushed against the skin (20, 22) such that the rim portion (14) applies sufficient pressure against the skin for holding the eye (12) open. Eyewash is delivered and drained to and from the chamber (45) by inlets (50, 52) and an outlet (60). The inlets and the outlets are interchangeable. Eyewash delivered into the chamber (45) is directed such that the flow of the eyewash first contacts a surface of the eye (12) which is spaced a distance from the corneal portion (70) of the eye and then flows over and across the entire eye.

9 Claims, 2 Drawing Sheets

Fig. 2
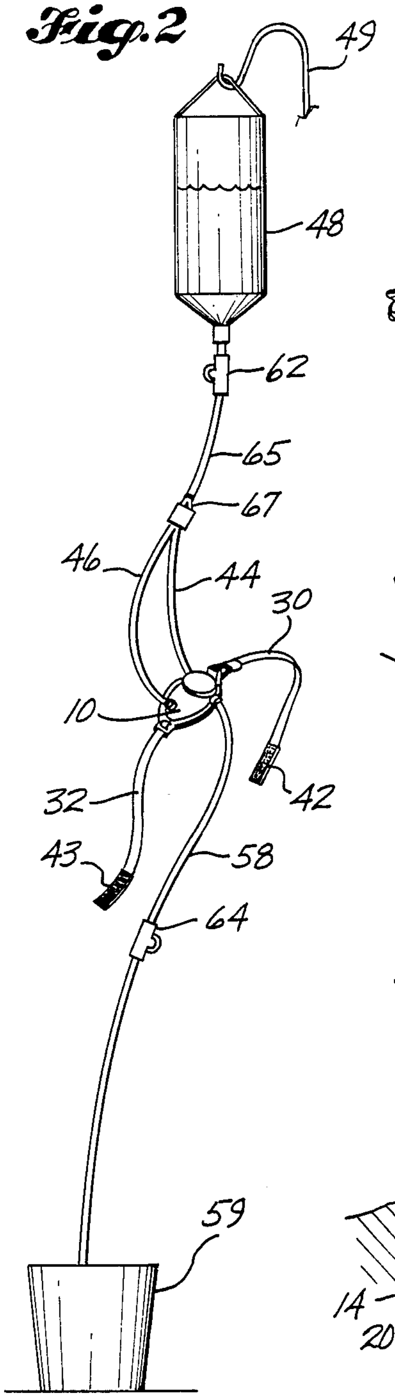
Fig. 3
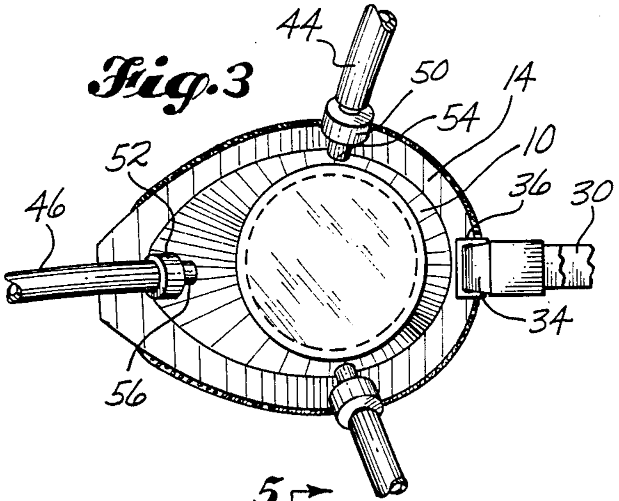
Fig. 4
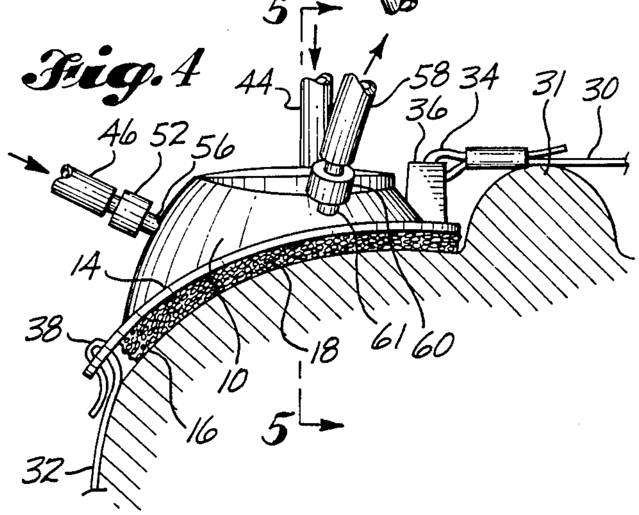
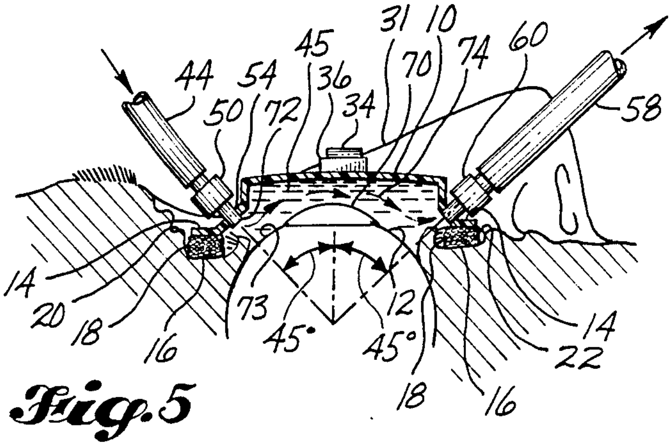
Fig. 5

EYE WASHING METHOD AND APPARATUS

TECHNICAL FIELD

This invention relates to the provision and use of an improved goggle type eyewashing device that is basically characterized by an eyecup adapted to hold the eye open during the eye washing operation, and a washing solution delivery system adapted to flow washing solution to and over the entire eye without inducing a corneal reflex or a blepharal spasm.

BACKGROUND ART

A common injury is the accidental introduction of foreign material into an eye. To date, the techniques for treating such an injury have various drawbacks. The most common form of treatment is an improvised method which consists of administering a liquid eyewash over the external surface of the eye by squirting an eyewash through a tube which extends from a bag of treatment solution. This method requires the person administering the eyewash to immobilize the eyelids with one hand, while holding the end of the tube with the other, and sweeping the eyewash across the eye until the entire surface of the eye is washed properly.

There are several disadvantages to this method. One disadvantage is that a patient tends to feel threatened by it. For an eye to be properly washed by the above method, it is generally required that the patient lie motionless in a recumbent position. It is difficult for the patient to do this when he is aware that he is about to undergo a rather uncomfortable process, i.e. having a fluid squirted into an eye. The eye is a sensitive organ and it is a natural reaction for the patient to try to protect the eye by either closing it or averting his head. The patient thus feels threatened by the above method, making it harder for him to remain motionless, with the resultant effect of making the eyewashing process more difficult.

Another disadvantage is that the technique described above requires an experienced person to administer the eyewash. This will usually be a medical person whose uninterrupted attention is required for eyewashing, making it impossible for him or her to treat other related injuries which possibly resulted from the same accident.

A further disadvantage is that drainage of the eyewash from the eye cannot be controlled. The eyewash can flow onto the face and clothing of the patient, and onto surrounding areas.

There are other, more innovative ways of treating an eye, such as the scleral lens disclosed in U.S. Pat. No. Re. 28,873, granted June 22, 1976 to Lorne B. Morgan. The lens employs a cup-like eye shield having a concave inner surface which overlies the front portion of the eye. However, the lens has many of the same drawbacks which were described above. For example, the lens must be used by a professionally trained individual. In addition, the lens does not enable the eye to be open while the lens is in use. Also, the system provides no way of controlling the drainage of the eyewash from the eye. Goggle type eyewashing devices are known. It is also known to use an eyecup placed over an eye as a method of confining an eyewash in a chamber for contacting the eye. It is also known to use tubing for delivering and draining eyewash to and from the chamber formed by the eyecup.

Prior art devices which are pertinent to the present invention are disclosed by the following United States patents:

U.S. Pat. No. 676,379, granted June 11, 1901 to Frank E. Young; No. 1,006,945, granted Oct. 24, 1911 to James D Houston; No. 1,246,971, granted Nov. 20, 1917 to Friedrich Maier; No. 1,362,682, granted Dec. 21, 1920 to Frank E. Dayton; No. 1,437,435, granted Dec. 5, 1922 to Friedrich Maier; No. 1,900,201, granted Mar. 7, 1933 to Solomon M. Sager; No. 2,524,720, granted July 24, 1946 to Charles A. Watrous; No. 2,818,068, granted Sept. 2, 1955 to Anthony De Felice; No. 3,261,355, granted Mar. 11, 1964 to Henry Burbig; No. 3,664,340, granted May 23, 1972 to Loran B. Morgan; No. 4,193,401, granted Mar. 18, 1980 to Rosolino Marinello; and U.S. Pat. No. Re. 28,873, granted June 22, 1976 to Loran B. Morgan.

Particularly pertinent to the present invention is Maier, U.S. Pat. No. 1,437,435. Although this patent, and the other above-cited patents, address some of the above discussed disadvantages to varying degrees, they fail to address a major problem associated with washing an eye.

When washing an eye, it is important to keep the eye open so that the eyewash contacts and covers as much surface of the eye as is possible. However, keeping the eye open is counter to the natural reaction a person has to close the eye when a foreign object or substance is introduced into it. Such a reaction is primarily involuntary because of the high sensitivity of the eye to contact.

The cornea region of the eye is particularly sensitive to contact. When the cornea is contacted by a foreign object or substance, such as for example, particles or dust or other particulate matter, a corneal reflex is induced causing a blepharal spasm. A blepharal spasm is a strong involuntary muscular reaction by the eye which reflexively closes the eye in response to the introduction of a foreign substance. It is not necessary that a particle contact the cornea region to induce a blepharal spasm. For example, applying eye drops to an eye directly on the pupil or iris can induce a blepharal spasm. Or, applying an eyewash by using one eyecup can also induce a blepharal spasm if the eyewash is applied improperly.

Therefore, for an eyecup to be effective in a method for washing an eye, it is desirable that it have two features. First, the eyecup should have the capability to hold the eye open while it is being washed. Second, the eyewash should be delivered into the chamber formed by the eyecup such that the eyewash does not induce a blepharal spasm. It is believed that none of the above-cited patents provide devices or methods which provide these two features.

The advantages of the present invention over the patents cited above will become apparent upon further reading of this application.

DISCLOSURE OF THE INVENTION

In basic form, the present invention provides a method for washing an eye. An eyecup having a rim portion that complementarily fits to the orbit portion which surrounds an eye on the face of a person is placed over the eye to form a liquid confining chamber. After the eyecup is in such position, the skin above and below the eye is drawn away from the eye. Then, the eyecup is pushed against said skin such that the rim portion puts pressure on said skin for holding the eye open. A liquid eyewash is then delivered into the liquid confining chamber and contacts the eye with the result that it produces a washing action enabling the eye to be either cleansed with water or treated with a medical solution. The eyewash is drained from the chamber such that a continuous flow of eyewash can pass through the chamber, if it is so desired.

As mentioned above, the rim portion of the eyecup complementarily fits to the orbit portion of the face which surrounds an eye. The rim portion has a skin-contacting surface that, when the eyecup is placed over the eye, puts pressure on the skin above and below the eye for holding the eye open. The rim portion may include a padding material which is both impermeable to the eyewash for providing such a skin-contacting surface and comfortable to the wearer.

Wall portions of the eyecup have at least one inlet and at least one outlet for delivering and draining eyewash to and from the liquid confining chamber. Each inlet directs the eyewash into the chamber such that the eyewash first contacts a side surface of the eye which is spaced a distance from both the iris and the pupil. This avoids stimulating a blepharal spasm in the eye.

One aspect of the present invention is that inlets may be interchanged with outlets. Certain embodiments of the invention utilize a single eyepiece. In these embodiments, the inlets can be interchanged with the outlets for enabling the eyecup to be rotated for use on either eye of the person being treated. Furthermore, after such an interchange, each of the inlets which formerly was an outlet is also directed for delivering eyewash a spaced distance from the iris and pupil portions of the eye.

The inlets and outlets are in the form of reduced internal diameter ends on the conduits which deliver and drain fluid to and from the liquid confining chamber formed by the eyecup. Each tube end is fixably insertable in apertures located in sidewall portions of the eyecup.

An advantage to the present invention is that it provides a method for holding and keeping an eye open during an eyewashing process. An eye has a tendency to involuntarily close in reflexive action when a foreign substance, such as an eyewash, is introduced into it. The skin-contacting surface on the rim portion of the eyecup holds the eye open while it is being washed, thus countering this tendency. In addition, the cornea region of the eye is particularly sensitive to the introduction of a foreign substance. Placing an eyewash directly on the cornea region can induce a corneal reflex with the resulting strong reflexive action by the eye muscles (blepharal spasms) causing the eye to close. Placing the eyecup inlets such that the cornea region is not first contacted by the eyewash minimizes the corneal reflex and blepharal spasms and keeps the eye open.

In preferred form, the inlets are located out of the line of sight of the patient, so that the patient is unaware of their location. This arrangement eliminates an anticipated corneal reflex. The inlets are directed generally normal to a side portion of the sclera and at about forty-five degrees (45°) to a line passing through the center of the eyeball and the center of the iris. The eyewash liquid, whether delivered through the top inlet or the side inlet, initially contacts the sclera which is not sensitive. As the eyewash liquid enters the eyecup it flows through the cup, from side-to-side or from top-to-bottom, over and along the surface of the eye. Liquid flow contacts and washes the entire surface of the eye.

These features, and others will become more apparent when the detailed description of the invention is read in conjunction with the drawings.

BRIEF DESCRIPTION OF THE DRAWINGS

In the drawings, like reference numerals refer to like parts throughout, and:

FIG. 2 is an elevational view of a complete eyewashing system including the eyecup of FIG. 1, and apparatus for delivering eyewashing solution to, and draining it from the eyecup;

FIG. 3 is a front elevational view of the eyecup of FIG. 1, with the face not shown, but showing the connection of eyewash delivery and drainage conduits in fragmentary form;

FIG. 4 is a side elevation view of the eyecup of FIG. 1, looking in a direction which is upward relative to the face, with portions of the face being shown in cross section, and eyewash delivery and drainage conduits being shown in fragmentary form;

FIG. 5 is a sectional view of the eyecup shown in FIGS. 1, 3, and 4, looking along line 5—5 of FIG. 4;

BEST MODE FOR CARRYING OUT THE INVENTION

Figure 1:
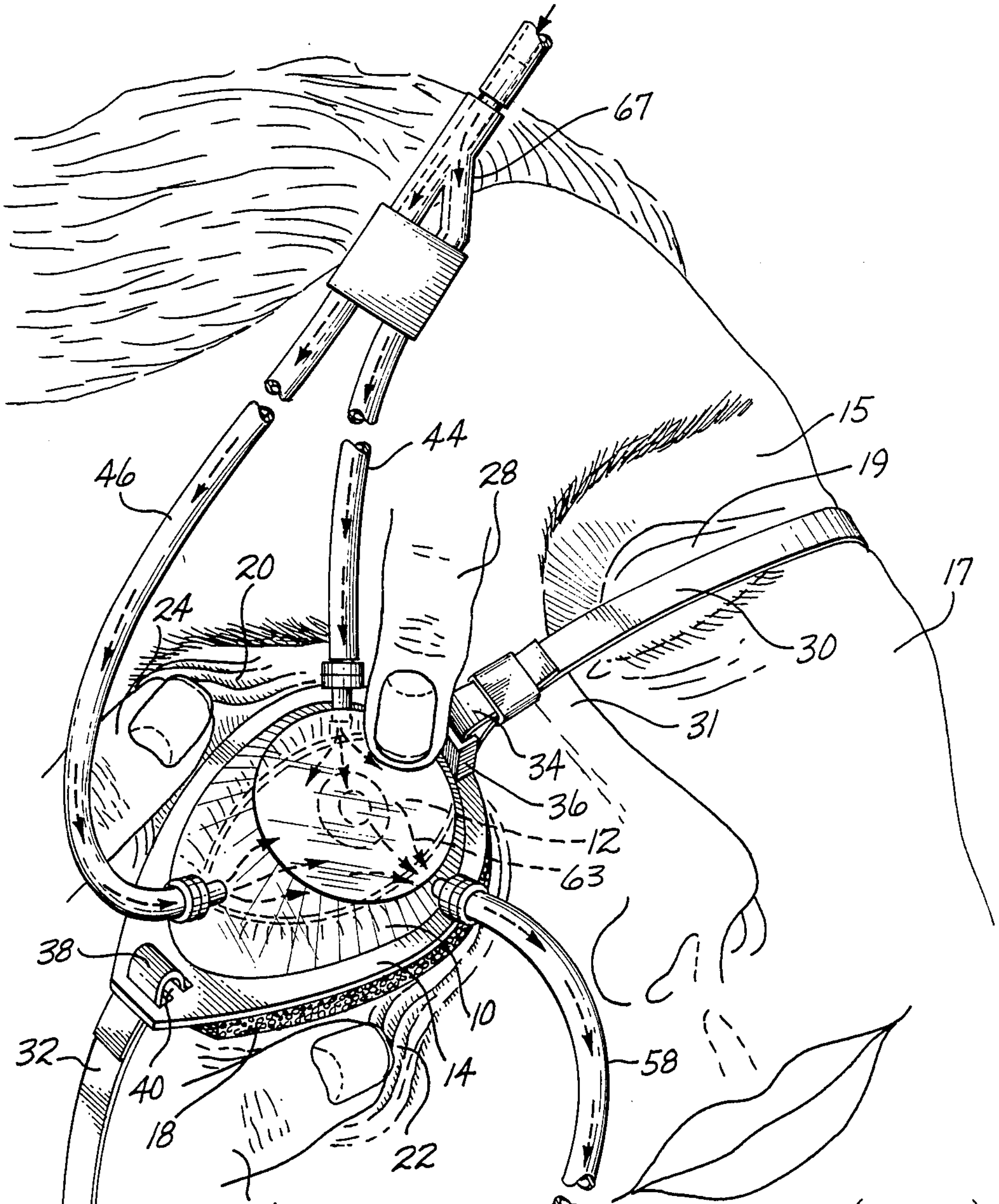
FIG. 1 is a pictorial view showing an embodiment of the invention positioned over an eye on the face of a person and being used for washing the eye.

Referring now to the drawings, and first to FIG. 1, a goggle-shaped eyecup 10 is shown being placed in position over an eye 12. The eyecup 10 has a rim portion 14 which includes a skin-contacting surface 16, which is best shown in FIG. 5. In preferred form, the eyecup 10 is made of a rigid transparent plastic material, and the skin-contacting surface 16 is composed of a soft padding material 18. The padding material 18 could be made of any foam material which is impermeable to a liquid eyewash, such as foam rubber, for example. The rim portion 14 and skin-contacting surface 16 are shaped such that they complementarily fit to an orbit portion 15 which surrounds either eye 12, 19 on the face 17 of a person.

To use the eyecup, a medical person or other user may first place the eyecup 10 over the eye 12. The skin above and below the eye, indicated by numerals 20 and 22, respectively, may then be simultaneously drawn apart and away from the eye by fingers 24 and 26. After drawing the skin 20, 22 apart, the eyecup 10 is pushed down by finger 28 such that the skin-contacting surface 16 applies pressure to the skin 20, 22 holding the skin such that the eye is kept open. FIG. 5 best shows the skin-contacting surface 16 holding the skin 20, 22 away from the eye 12.

Once the eyecup 10 has been properly positioned by the fingers 24, 26, 28, two elastomeric straps 30, 32, fastened to the eyecup 10, hold it in place over the eye 12. Strap 30 is attached to the eyecup 10 by a loop 34 connected to a strap post 36. As is shown in FIG. 4, loop 34 is connected to strap post 36 at a sufficiently high position relative to the bridge of the nose 31 such that the nose cannot cause the strap 30 to pull the eyecup 10 upwardly away from the face 17. Strap 32 is connected to the eyecup 10 by means of a loop 38 which is passed through two slots 40 located in the rim portion 14 of the eyecup 10. The straps 30, 32 each extend around the head of the person to the back fo the head where they are joined together by means of velcro fasteners 42 and 43 (See FIG. 2). Tension in the straps 30, 32 may pull the eyecup 10 down over the eye 12 such that sufficient pressure is maintained by the skin-contacting surface 16 against the skin 20, 22 to hold the eye open. Or, inward finger pressure may be maintained on the eyecup, pressing in against the stretched skin, to keep the skin stretched and the eye open.

There are other ways of preparing the apparatus for use. For example, the eyecup may be first strapped in place on the patient and then the skin regions 20, 22 drawn apart, followed by an inward force being applied to the eyecup for the purpose of holding the skin in position and the eye open.

After the eyecup 10 has been placed in operative position, as in the manner described above, the eye 12 is then ready to be washed. When positioned over the eye 12, the eyecup 10 forms a liquid confining chamber 45 (See FIG. 5) adjacent the eye. Liquid eyewash is delivered into the chamber 45 by means of eyewash delivery conduits 44 and 46. These delivery conduits 44, 46 are connected to a source of eyewash, such as a bag of physiologic solution 48 shown hanging from a support 49 in FIG. 2. The delivery conduits 44, 46 are connected to the eyecup 10 by inlet members 50 and 52, shown in FIG. 6 in the form of separate members fitted into the tubing ends. These members 50, 52 may be inserts having nipple ends 51, 52 (FIG. 6) which are fixably insertable into apertures 54, 56 located in sidewall portions of the eyecup 10.

Eyewash is drained from the chamber by a drainage conduit 58. The drainage conduit 58 is connected to the eyecup 10 in a manner which is similar to the connection of the delivery conduits 41, 46 to the eyecup. Another end member 60, connected as an outlet to conduit 58, and including a nipple end 59, is fixably inserted into an aperture 61 in a sidewall portion of the eyecup 10. The drainage conduit 58 removes eyewash from the chamber and carries it to a sink or bucket 59 (See FIG. 2) for disposal of the eyewash solution.

In preferred form, aperture 54 is located in an upper sidewall portion of eyecup 10, aperture 56 is located in an end sidewall portion of eyecup 10, and aperture 61 is located in the lower sidewall portion of eyecup 10. Having the apertures 54, 56, 61 in such locations places them in close proximity to upper, end, and lower portions of the eye 12, respectively. This configuration enables the members 50, 52, and 60 to deliver and drain eyewash from the chamber 45 in a swirling action as indicated by the dashed arrows 63 shown in FIG. 1.

Figure 6:
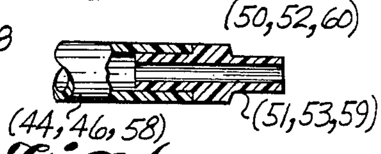
FIG. 6 is a fragmentary sectional view of one of the tube ends, showing an end fitting connected to the tubing.
Figure 7:
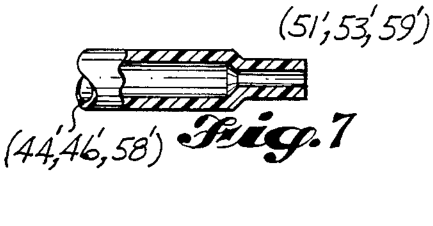
FIG. 7 is a view like FIG. 6, but of a reduced diameter end portion which is an integral part of the tubing.

As shown by FIG. 7, the nipple ends 51', 53', 59' may be integral end portions of the tubing 44', 46', 58'. As shown by FIGS. 5 and 6, regardless of the manner in which the nipple ends are formed, such ends have reduced diameter passageways in comparison with the inside diameter of the tubing. As a result, there is an increase in velocity of the eyewash liquid as it flows through the inlet members. The reduced diameter in the outlet member retards flow out from the eyecup chamber.

The flow of the eyewash into and out of the chamber 45, as shown by arrows 65 in conduits 44, 46, and 58, can be controlled by valves 62 and 64. One value 62 is located between the bag of physiologic solution 48 and the eyecup 10, as shown in FIG. 2. Valve 62 is connected in a single conduit 65 for controlling eyewash flow to the eyecup 10. The conduit 65 has a standard "Y" type connector 67, which divides the conduit 65 into the two delivery conduits 44 and 46. The other valve 63 is located in conduit 58 between the eyecup 10 and a sink or the bucket 59.

By way of example only, FIG. 1 shows a suitable form of construction for valve 64 which is appropriate for use with this invention. The valve 64 is composed of a channel member 66 having an eccentric rotatable cam 68 axially mounted such that the cam rotates in the channel. Drainage conduit 58 runs through the channel 66 adjacent the cam 68. By rotating the cam 68, pressure can be placed against the conduit 58 variably squeezing it to control flow. The cam 68 is held in a particular position by friction between the side of the cam and the inside walls of the channel 66.

Having valves 62, 64 located above and below the eyecup 10, as is shown in FIG. 2, allows the user of the invention to have two independent points of control for governing eyewash flow into and out of the chamber 45 formed by the eyecup 10. Thus, if it is desired to do so, the user can either maintain a steady flow of eyewash through the chamber 45, or the eyewash can be stagnated adjacent the eye 12 by opening valve 62 and closing valve 64.

As was mentioned previously, members 50, 52 deliver eyewash into the chamber 45 adjacent the eye 12. The inlet members 50, 52 are inserted through apertures 54 and 56, respectively. They are positioned in these apertures such that eyewash is directed into the chamber against the surface of the eye 12 at a distance which is spaced from the iris and pupil portions 70 of the eye. Referring specifically to member 50 in FIG. 5, directing the eyewash into the chamber 45 at such a spaced distance is accomplished by having the end 72 of inlet member 50 positioned so that the eyewash first contacts the edge 73 of the eye. The eyewash flows over the iris and pupil 70 (in the direction indicated by arrow 74) and out of the chamber through nozzle member 60. By not having the eyewash enter the chamber 45 directly on the iris and pupil 70, the possibility of inducing a blepharal spasm in the eye is substantially reduced. This is important because the pressure of skin-contacting surface 16 against the skin 20, 22 may not be sufficient to hold the eye open in the event of a strong blepharal spasm.

The inlet members 50, 52 can be easily inserted into and removed from apertures 54 and 56. Likewise, outlet member 60 can be easily inserted into and removed from aperture 61. This enables either delivery conduit 44 or 46 to be interchanged with drainage conduit 58. The advantage to this feature is that it enables the eyecup 10 to be switched from eye to eye. For example, by switching inlet member 50 with outlet member 60, the eyecup 10 is then ready for placement over the other eye of the patient. Outlet member 60 would then function in exactly the same manner as inlet member 50 previous to the interchange, with member 60 delivering eyewash into the chamber at a distance which is spaced from the pupil and iris portions 70 of the eye. It should be noted, however, that as an alternative to switching a single eyecup, another eyecup could be employed making a pair of eyecups for washing both eyes simultaneously.

In preferred form, the inlets are located out of the line of sight of the patient, so that the patient is unaware of their location. This arrangement eliminates an anticipated corneal reflex. The inlets are directed generally normal to a side portion of the sclera and at about forty-five degrees (45°) to a line passing through the center of the eyeball and the center of the iris (FIG. 5). The eyewash liquid, whether delivered through the top inlet or the side inlet, initially contacts the sclera which is not sensitive. As the eyewash liquid enters the eyecup it flows laterally of the cup, from side-to-side or from top-to-bottom, over and along the surface of the eye. Liquid flow contacts and washes the entire surface of the eye.

The above description is to be interpreted only in the sense that it describes the best mode for carrying out the invention. It is apparent that changes in the invention, not included in the above description, could be made without departing from the spirit and scope of the invention. It is intended that the scope of the invention shall be limited only by the appended claims which follow.

What is claimed is:

1. A method for washing an eye comprising:
providing an eyecup having a rim portion that complementarily fits to the orbit portion which surrounds an eye on the face of a person;
placing the eyecup over the eye to form a liquid confining chamber adjacent the eye;
drawing the skin above and below the eye away from the eye;
pushing the eyecup against the skin such that the rim portion of the eyecup puts pressure on said skin above and below the eye for holding the eye open;
delivering liquid eyewash into the chamber and against a surface of the eye which is spaced a distance from the corneal portion of the eye to produce a washing action; and
draining the eyewash from the chamber.

2. The method according to claim 1 including:
delivering the eyewash into the chamber through at least one inlet in a wall portion of said eyecup; and
draining the eyewash from the chamber through at least one outlet in a wall portion of said eyecup.

3. The method according to claim 2 including:
delivering the eyewash into the chamber through two inlets in a wall portion of said eyecup, one of which is located above the eye and the other of which is located at the outer side of the eye.

4. An apparatus for washing an eye comprising:
an eyecup which forms a liquid confining chamber adjacent an eye, said eyecup having a rim portion that complementarily fits to the orbit portion which surrounds an eye on the face of a person, said rim portion having a skin-contacting surface constructed so that, when said eyecup is placed over an eye, and is pushed in towards the eye, said rim portion will put pressure on the skin above and below the eye for holding the eye open, said eyecup further having at least one inlet in a wall portion of said eyecup for delivering eyewash to said chamber directly against the eye, and at least one outlet in a wall portion of said eyecup for draining eyewash from said chamber wherein said inlet is directed for delivering eyewash into the chamber such that the eyewash first contacts a surface of the eye which is spaced a distance from the corneal portion of the eye.

5. An apparatus in accordance with claim 4, wherein said rim portion includes a soft padding material which is impermeable to the eyewash.

6. An apparatus in accordance with claim 5, wherein said eyecup includes an upper sidewall portion, a lower sidewall portion, and an end sidewall portion, each sidewall portion being in proximity to an upper, a lower, and a side portion of an eye, respectively, with a first inlet being located in said upper sidewall portion, and a second inlet being located in said end sidewall portion, and said outlet being located in said lower sidewall portion, and further, said first inlet being interchangeable with said outlet thereby enabling a single eyecup to be switched for use on either eye of a person.

7. An apparatus in accordance with claim 6, wherein said first and second inlets, and said first outlet each comprise a conduit end which is fixably insertable in an aperture in each of said sidewall portions.

8. An apparatus in accordance with claim 7, wherein each conduit end has a reduced diameter passageway so that eyewash flowing through the inlets is formed into an incresed velocity stream and flow out from the cup through the outlet is retarded.

9. An apparatus in accordance with claim 5, wherein said inlet is directed generally normal to a side portion of the sclera and at about forty-five degrees (45°) to a line passing through the center of the eyeball and the center of the iris.

* * * * *

UNITED STATES PATENT AND TRADEMARK OFFICE

CERTIFICATE OF CORRECTION

PATENT NO. : 4,798,599

DATED : January 17, 1989

INVENTOR(S) : George Thomas

It is certified that error appears in the above-identified patent and that said Letters Patent is hereby corrected as shown below:

Column 5, line 3, "fo" should be -- of --.

Column 5, line 31, "ends 51, 52" should be -- ends 51, 53 --.

Column 6, line 5, "valve 63" should be -- valve 64 --.

Claim 8, column 8, line 40, "incresed" should be -- increased --.

Claim 9, column 8, line 42, "claim 5" should be -- claim 4 --.

Signed and Sealed this

Twenty-eighth Day of November 1989

Attest:

JEFFREY M. SAMUELS

*Attesting Officer* *Acting Commissioner of Patents and Trademarks*